United States Patent [19]

Krieger

[11] 4,239,036
[45] Dec. 16, 1980

[54] SURGICAL RETRACTOR

[76] Inventor: Abbott J. Krieger, 49 Nottingham Rd., Short Hills, N.J. 07078

[21] Appl. No.: 43,449

[22] Filed: May 29, 1979

[51] Int. Cl.³ ............................................. A61B 17/02
[52] U.S. Cl. ...................................................... 128/20
[58] Field of Search ...................... 128/3, 4, 15, 16, 20, 128/341, 343, 345, DIG. 9, 6; 248/274, 276, 160; 64/6, 7

[56] References Cited

U.S. PATENT DOCUMENTS

| | | | |
|---|---|---|---|
| 1,460,697 | 7/1923 | Bendlin | 128/20 |
| 3,542,015 | 11/1970 | Steinman | 128/20 |
| 3,584,822 | 6/1971 | Oram | 248/276 X |
| 3,858,578 | 1/1975 | Milo | 128/20 |

OTHER PUBLICATIONS

Yasargil, "Leyla Brain Retractor", Catalog: *Instruments for Surgery & Micro Surgery*, Holco Inst. Corp., pp. 145-146, (1971).

*Primary Examiner*—Robert W. Michell
*Assistant Examiner*—Michael H. Thaler
*Attorney, Agent, or Firm*—Popper & Bobis

[57] ABSTRACT

A surgical retractor wherein a plurality of segments are strung together on a strand which may be tensioned; the segments are separated from each other by spacers also strung on the strand; the mating surfaces of the segments are concave and the intervening spacers are convex; tensioning of the strand causes the segments and spacers to frictionally engage each other and rigidize the attitude of the segments with respect to each other.

4 Claims, 7 Drawing Figures

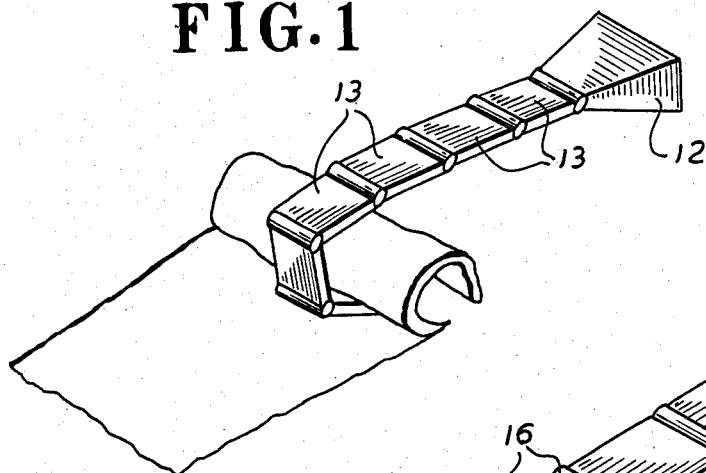
FIG. 1
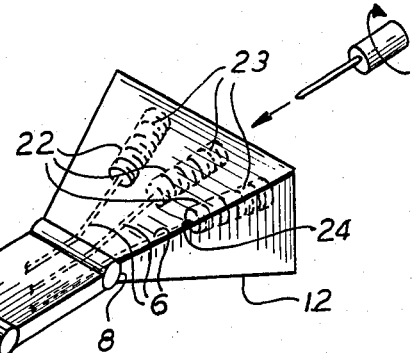
FIG. 2
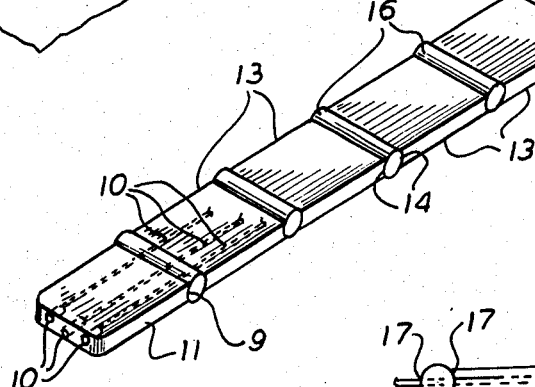
FIG. 3
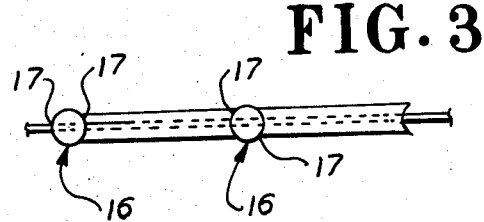
FIG. 4
FIG. 5
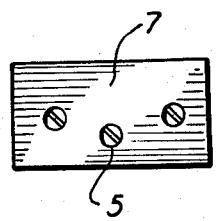
FIG. 7
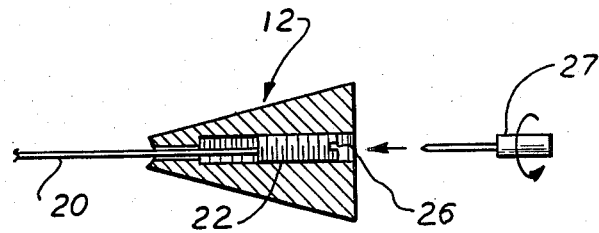
FIG. 6

SURGICAL RETRACTOR

BACKGROUND OF THE INVENTION

1. Field of the Invention

This invention relates generally to surgical retractors and particularly to segmented surgical retractors wherein the segments and intervening spaces are strung on a strand and rigidize as to position by the tensioning of the strand.

2. Prior Art

In the performance of various surgical acts, bodily tissues are cut but not severed from the bodily structure, to be restored after surgery is complete by sutures. While the tissues remain cut but unsutured, it is necessary that they be diverted from the site of the surgery and to this end, various retractors have been devised to hold surrounding tissues away from the site of the surgery and to keep that site unobstructed. There are integral deformable pieces, usually metal, which are non-resilient and may be bent to various shapes to retain tissues in unobstructing relationship to the site of the operation. There are segmented retractors that may function in a similar way. These devices frequently are not as completely self-sustaining as might be desired and after a period of time, they relax their tension on the retracted tissues and permit those retracted tissues to encroach upon the site of the operation, thereby making the work of the surgeon difficult, and requiring the readjustment of the retractor or the application of additional retractors, sometimes requiring the complete reapplication of the retractor.

SUMMARY OF THE INVENTION

It has been found that an articulated retractor can be provided which may be selectively required to assume numerous attitudes, one of which may be best suited to retracting tissues from the site of the operation. This retractor having been adjusted to the particular position best calculated to retract tissue from the site of an operation, may be made exceedingly rigid. This is accomplished by tensioning a strand which passes through the segments of the retractor and as well through spaces between the segments so as to frictionally engage them together against movement with respect to each other.

THE DRAWINGS

These objects and advantages as well as other objects and advantages may be obtained by the device shown by way of illustration in the drawings in which:

FIG. 1 is a perspective view of the surgical retractor rigidized to retract and hold a flap of tissue away from the site of surgery;

FIG. 2 is a perspective view of the retractor in normal linear position, showing the strands passing through the segments and the tensioning means in the rear end segment;

FIG. 3 is a partial vertical sectional view of several spaces and segments with the strand passed through them;

FIG. 4 is a perspective view of a segment, showing the opposite concave transverse engaging portions;

FIG. 5 is a perspective view of a spacer showing the passages therethrough for strands;

FIG. 6 is a vertical sectional side view of the rear end segment of the retractor; and FIG. 7 is a vertical elevational view of the rear end segment of the retractor.

PREFERRED EMBODIMENT

Referring now to the drawings in detail, the surgical retractor embodying the invention provides a front end segment 11. This is a generally rectangular element having a plurality of three longitudinal passages 10 therethrough. The inner end of the front end segment 11 is provided with a concave transverse surface 9. There is a rear end segment 12 having a generally pyramidal shape. The rear end segment 12 is provided with a longitudinal concave surface 8 and a flat base 7. As is the case with the front end segment 11 there are three passages 6 through the rear end segment commencing at the concave longitudinal surface 8 and extending to the base 7. Between the front end segment 11 and the rear end segment 12, there are a plurality of generally rectangular intermediate segments 13 each of which also have longitudinal passages 10. The intermediate segments 13 at their end portions adjacent to the other segments, 11, 12, 13, have transverse concavities 14. The segments 11, 12, 13 are preferably made of metal which makes them resistant to high heat necessary for sterilization. Of the metals, stainless steel is preferred. However, the retractor may also be made of plastic materials which would be resistant to destruction under high temperatures necessary for sterilization. Teflon is a suitable material. A plurality of generally rod shaped spacers 16 are interposed between the front end segment 11, the rear end segment 12 and the intermediate segments 13. These spacers 16 may also be made of metal such as stainless steel or may be made of a temperature resistant plastic material such as Teflon. It is preferred that the spacers 16 have a high coefficient of friction so that they are resistent to slipping when forcibly engaged with an adjacent segment. The spacers have externally transverse convex surfaces 17 so as to mate with the concavities 18 of the segments 13 and of the segments 11, 12. By way of illustration, all of the segments 11, 12, 13 and the spaces 16 are provided with three passages 10 which are arranged in general registration with each other to form a continuous passage from the front end segment 11 through the intermediate segments 13 through the spacers 16 and through the rear end segment 12. These passages 6, 10, 19 are larger than a strand 20 which passes through them; being larger, they allow for deflection of the segments 11, 12, 13 with respect to each other. If the passages were in exact conformity with the strands 20, the deflection of the segments with respect to each other would be overcome when tension was exerted upon the strands 20. With the passages 6, 10, 19 larger than the strand 20, deflection of the segments 11, 12, 13 from linearity to arcuate position is permitted. The longitudinal passages 19 in the spacers 16 are disposed in registration with the longitudinal passages 6, 10 in the segments 11, 12, 13. Of these passages 6, 10, 19, one passage 5 is preferably offset from the others as will appear in FIGS. 4 and 7. The rear end segment 12 is provided with threaded passages 22. A threaded plug 23 is engaged with each of the threaded passages 22. Strands 20 are passed through the threaded passages 22, through the intermediate segments 13, through the spaces 16 and to the front end segment 11 where the ends of the strands 20 are rigidly secured in the passages 10 in the front end segment 11. In the case of a metal segment, the ends of the strands may be anchored in the front end segment by welding, soldering, or by some cement which is sufficiently resistent to conditions of ordinary usage. The other end of the strands 20 are attached to threaded plugs 23 which are in threaded engagement with the threaded passage 22 in the rear end segment 12. This attachment of the strand 20 at its end 24 to the threaded plug 23 may be made by inserting it in a hole in the plug and soldering, welding or adhesively securing it therein. The head of the plug 25 may be provided with a slot 26 for the application of a screwdriver 27 to enable the plug 25 to be rotated to tension the strand and draw the segments 11, 12, 13 and the spacers 16 into tight frictional engagement with each other. In lieu of the slot and screwdriver method of rotating the plugs 25, any other means of adjustment may be provided such as a socket and a wrench. The strand 20 is preferably made of a multi-filament metal cable which may be subject to twisting without destruction. Other strands made of other material such as nylon or other plastic materials may be utilized.

Upon the tensioning of the strand, the various convexities 14 and concavities 18 will be brought together into frictional engagement with each other and this will rigidize the attitude of the segments 11, 12, 13 to each other in their engagement with spacers 16 to serve as a hook, as indicated in FIG. 1; in this manner, tissues or organs may be held away from the site of surgery. By relaxing the tension on the strand 20 by counterrotating the plug 23, the strand releases the tension on the segments 11, 12, 13 and the spacers 16 so that the retractor becomes limp.

What is claimed is:

1. A surgical retractor comprising,
   (a) a front end segment,
   (b) a rear end segment,
   (c) a plurality of intermediate generally rectangular segments disposed successively between the front end and the rear end segments.
   (d) opposing portions of the intermediate segments adjacent to each other provided with transverse concavities,
   (e) a longitudinal passage through the segments,
   (f) a plurality of rod shaped spacers disposed between the intermediate segments,
   (g) the spacers having transverse convexities in general conformity with the concavities of the adjacent intermediate segments,
   (h) the spacers having longitudinal passages therethrough in general registration with the longitudinal passages in the intermediate segments,
   (i) a stand,
   (j) the intermediate segments in alternation with the spacers strung on the strand with their respective concavities and convexities in engagement with each other,
   (k) the strand anchored at one end to the front end segment,
   (l) the passage in the rear end segment having a threaded portion,
   (m) a threaded plug in threaded engagement with the threaded passage in the rear end segment,
   (n) the strand anchored at its other end from the front end segment to the plug,
   (o) the threaded plug rotatable to exert or relax tension on the strand on which the intermediate segments and spacers are strung,
   (p) the tensioning of the strand engaging the convexities and concavities into frictional engagement wih the spacers intervening between the intermediate segments, to rigidize the attitude of the segments to each other in a preselected shape in which the intermediate segments have been deflected,
   (q) the relaxing of tension on the strand releasing the frictional engagement of the intermediate segments and spacers with each other until the segments become limp.

2. A surgical retractor in accordance with claim 1 in which the passages through the front end, rear end, and intermediate segments and the spacers are larger than the cross-sectional diameter of the strand.

3. A surgical retractor in accordance with claim 1 in which the spacers are composed of a material having a high coefficient of friction.

4. A surgical retractor in accordance with claim 1 comprising,
   (a) a means to rotate the threaded plug to exert tension or relax tension on the strand.

* * * * *